United States Patent

Breitscheidel et al.

[11] Patent Number: 5,874,622
[45] Date of Patent: Feb. 23, 1999

[54] HYDROGENATION OF AN AROMATIC COMPOUND IN THE PRESENCE OF A SUPPORTED CATALYST

[75] Inventors: Boris Breitscheidel, Limburgerhof; Thomas Rühl, Frankenthal; Klemens Flick, Herxheim; Jochem Henkelmann, Mannheim; Andreas Henne, Neustadt; Rolf Lebkücher, Mannheim, all of Germany

[73] Assignee: BASF Aktiengesellschaft, Ludwigshafen, Germany

[21] Appl. No.: 987,781

[22] Filed: Dec. 9, 1997

[30] Foreign Application Priority Data

Dec. 9, 1996 [DE] Germany ............. 196 51 129.1

[51] Int. Cl.⁶ ................................. C07C 209/72
[52] U.S. Cl. ............. 564/450; 564/451; 568/834
[58] Field of Search .................. 564/450, 451; 568/834

[56] References Cited

U.S. PATENT DOCUMENTS

| | | |
|---|---|---|
| 2,606,925 | 8/1952 | Whitman . |
| 2,822,392 | 2/1958 | Illich et al. . |
| 2,927,127 | 3/1960 | Somerville et al. . |
| 3,520,928 | 7/1970 | Greco . |
| 3,591,635 | 7/1971 | Farrissey et al. . |
| 3,636,108 | 1/1972 | Brake . |
| 3,697,449 | 10/1972 | Brake . |
| 4,155,694 | 5/1979 | Savioli . |
| 4,343,955 | 8/1982 | Oshima et al. . |
| 4,384,142 | 5/1983 | Merten et al. . |
| 4,429,155 | 1/1984 | Goetz et al. . |
| 4,551,564 | 11/1985 | Otte et al. . |
| 4,914,239 | 4/1990 | Kiyuma et al. . |
| 4,952,549 | 8/1990 | Immel et al. . |
| 5,322,965 | 6/1994 | Immel et al. . |
| 5,516,851 | 5/1996 | Flick et al. .............. 525/330 |

FOREIGN PATENT DOCUMENTS

| | | |
|---|---|---|
| 324190 | 7/1989 | European Pat. Off. . |
| 2132547 | 6/1971 | Germany . |
| 224315 | 4/1984 | Germany . |
| 19533718 | 9/1995 | Germany . |
| 19604791 | 2/1996 | Germany . |
| 19616822 | 4/1996 | Germany . |
| 19622705 | 6/1996 | Germany . |
| 7019901 | 7/1967 | Japan . |
| 7235424 | 10/1968 | Japan . |
| 59-196843 | 4/1983 | Japan . |
| 137526 | 12/1982 | Poland . |

*Primary Examiner*—Brian M. Burn
*Attorney, Agent, or Firm*—Keil & Weinkauf

[57] ABSTRACT

In a process for hydrogenating an aromatic compound in which at least one hydroxyl group is bonded to an aromatic ring or an aromatic compound in which at least one amino group is bonded to an aromatic ring, in the presence of a catalyst comprising as catalytically active component at least one metal of transition group I, VII or VIII of the Periodic Table applied to a support, the catalyst is obtainable by a) dissolving the catalytically active component or a precursor compound thereof in a solvent, b) admixing the solution thus obtained with an organic polymer which is able to bind at least ten times its own weight of water, giving a swollen polymer, c) subsequently mixing the swollen polymer with a catalyst support material and d) shaping, drying and calcining the composition obtained in this way.

6 Claims, No Drawings

HYDROGENATION OF AN AROMATIC COMPOUND IN THE PRESENCE OF A SUPPORTED CATALYST

The present invention relates to a process for hydrogenating an aromatic compound in which at least one hydroxyl group is bonded to an aromatic ring or an aromatic compound in which at least one amino group is bonded to an aromatic ring, in the presence of a catalyst comprising as catalytically active component at least one metal of transition group I, VII or VIII of the Periodic Table applied to a support.

In one embodiment, the present invention relates to a process for hydrogenating an aromatic compound in which at least one hydroxyl group is bonded to an aromatic ring and preferably, in addition to at least one hydroxyl group, at least one unsubstituted or substituted $C_1$–$C_{10}$-alkyl group and/or at least one $C_1$–$C_{10}$-alkoxy group is bonded to an aromatic ring. Furthermore, preference is given to using monoalkyl-substituted phenols in the process of the present invention.

The monocyclic or polycyclic aromatic compounds are hydrogenated in the presence of the catalyst described herein to give the corresponding cycloaliphatic compounds, with the hydroxyl group being retained.

Cycloaliphatic alcohols, in particular alkylcyclohexanols, are important intermediates for the preparation of various fragrances, drugs and other organic fine chemicals. The abovementioned cycloaliphatic alcohols are conveniently obtained by catalytic hydrogenation of the corresponding aromatic precursors.

The process for preparing alkylcyclohexanols by catalytic hydrogenation of the corresponding alkylphenols is known. The hydrogenation of alkylphenols to give the corresponding alkylcyclohexanols in the presence of hydrogenation catalysts, in particular catalysts applied to supports, has been described many times.

Catalysts used are, for example, metallic rhodium, rhodium-platinum alloys, rhodium-ruthenium alloys and also ruthenium, palladium or nickel on catalyst supports. Catalyst supports used are carbon, barium carbonate and in particular aluminum oxide.

PL 137 526 describes the hydrogenation of p-tert-butylphenol to give p-tert-butylcyclohexanol using a nickel catalyst.

DE-A-34 01 343 and EP 0 141 054 describe a process for preparing 2- and 4-tert-butylcyclohexanol from 2- and 4-tert-butylphenol by catalytic hydrogenation. The hydrogenation is carried out in two stages, using a palladium catalyst on an $Al_2O_3$ support in the first stage and using a ruthenium catalyst on an $Al_2O_3$ support in the second stage. The metal content on the support is here from 0.1 to 5% by weight. The supports are not specified further. The reaction is carried out at a pressure of 300 bar with recirculation of product, and the cis-tert-butylcyclohexanols are obtained preferentially, with from 0.1 to 0.5% of by-products being formed.

U.S. Pat. No. 2,927,127 describes a process for preparing p-tert-butylcyclohexanol and esters thereof by catalytic hydrogenation of p-tert-butylphenol. Catalysts used are 5% rhodium on carbon, 5% palladium on barium carbonate and 5% ruthenium on carbon. When using ruthenium on carbon, the reaction was carried out at from 74° to 93° C. and a pressure of from 70 to 120 bar. 66% of the cis isomer were obtained as hydrogenation product.

DE-A-29 09 663 describes a process for preparing cis-alkylcyclohexanols by catalytic hydrogenation of the corresponding alkylphenols. The catalyst used was ruthenium on an $Al_2O_3$ support and the reaction was carried out at a pressure of 40, 60 or 80 bar. The products obtained were predominantly cis-alkylcyclohexanols, with from 0.1 to 1% of alkylbenzenes being formed as by-product.

In a further embodiment, the present invention relates to a process for hydrogenating an aromatic compound in which at least one amino group is bonded to an aromatic ring and preferably, in addition to at least one amino group, at least one unsubstituted or substituted $C_1$–$C_{10}$-alkyl group and/or at least one $C_1$–$C_{10}$-alkoxy group is bonded to an aromatic ring. Particular preference is given to using monoalkyl-substituted amines.

The monocyclic or polycyclic aromatic compounds are hydrogenated in the presence of the catalyst described herein to give the corresponding cycloaliphatic compounds, with the amino group being retained.

Cycloaliphatic amines, in particular unsubstituted or substituted cyclohexylamines and dicyclohexylamines, are used for preparing ageing inhibitors for rubbers and plastics, as corrosion inhibitors and also as precursors for crop protection agents and textile auxiliaries. Cycloaliphatic diamines are additionally employed in the production of polyamide and polyurethane resins and are also used as hardeners for epoxy resins.

It is known that cycloaliphatic amines can be prepared by catalytic hydrogenation of the corresponding monocyclic or polycyclic aromatic amines. The hydrogenation of aromatic amines to give the corresponding cycloaliphatic amines in the presence of hydrogenation catalysts, particularly catalysts applied to supports, has been described many times.

Catalysts used are, for example, Raney cobalt with additions of basic compounds (JP 43/3180), nickel catalysts (U.S. Pat. No. 4,914,239, DE 80 55 18), rhodium catalysts (BE 73 93 76, JP 70 19 901, JP 72 35 424) and palladium catalysts (U.S. Pat. No. 3,520,928, EP 501 265, EP 53 818, JP 59/196 843). However, ruthenium-containing catalysts are used in the majority of cases.

DE 21 32 547 discloses a process for hydrogenating monocyclic or polycyclic aromatic diamines in the presence of a suspended ruthenium catalyst to give the corresponding cycloaliphatic amines.

EP 67 058 describes a process for preparing cyclohexylamine by catalytic hydrogenation of the corresponding aromatic amine. The catalyst used is ruthenium metal in finely divided form on activated aluminum pellets. After four recirculations, the catalyst began to lose its effectiveness.

EP 324 984 relates to a process for preparing a mixture of unsubstituted or substituted cyclohexylamine and unsubstituted or substituted dicyclohexylamine by hydrogenation of unsubstituted or substituted aniline using a catalyst comprising ruthenium and palladium on a support and further comprising an alkaline alkali metal compound as modifier. A process which is similar in principle is described in EP 501 265 where the catalyst contains niobic acid, tantalic acid or a mixture of the two as modifier.

U.S. Pat. No. 2,606,925 describes a process for preparing an aminocyclohexyl compound by hydrogenating a corresponding aromatic compound using a ruthenium catalyst whose active catalytic component is selected from among elemental ruthenium, ruthenium oxides and ruthenium salts in which the ruthenium is present in the anion or in the cation. As the examples of this process show, here too, the catalyst is prepared in a separate step, dried and after a prolonged drying time introduced into the reaction vessel.

A further process for preparing cyclohexylamine is described in U.S. Pat. No. 2,822,392. This patent mainly addresses the use of a specific reactor in which the aniline and the hydrogen as starting materials are reacted with one another in countercurrent.

U.S. Pat. No. 3,636,108 and U.S. Pat. No. 3,697,449 concern the catalytic hydrogenation of aromatic, nitrogen-containing compounds using a ruthenium catalyst which further comprises an alkali metal compound as modifier.

In many of the above-described processes, it has been found to be a disadvantage that these reactions not infrequently resulted in relatively large amounts of alkylbenzenes as well as further, unidentifiable compounds which are formed in the hydrogenation as decomposition products or by-products. These by-products make the work-up and purification of the reaction product more difficult, particularly when, for example, alkylcyclohexanols are to be used as fragrances or for the preparation of fragrances. Furthermore, the activity of many of the catalysts used in the processes described above decreases quickly, particularly when the hydrogenation is carried out at relatively high reaction temperatures to accelerate the reaction rate.

The Applicant itself has submitted a series of recent Patent Applications, DE 196 04 791.9, DE 195 33 718.2, DE 196 24 484.6, DE 196 24 485.4, DE 196 16 822.8, DE 196 22 705.4, which all concern processes of the type being considered here for using specific supported catalysts comprising ruthenium and possibly further metals of transition groups I, VII and VIII of the Periodic Table. These processes for hydrogenating aromatic compounds as defined above make it possible to obtain the corresponding hydrogenated aromatic compounds in very high yield or at virtually complete conversion with a simultaneously only minimal proportion of by-products.

It is an object of the present invention to provide a further process for hydrogenating an aromatic compound as defined in the introduction which enables very high yields or virtually complete conversion to be achieved. Furthermore, this process should make it possible to obtain the desired products with an only minimal proportion of by-products or decomposition products and the process should be carried out at high throughputs over the catalyst and long operating lives with an extremely high turnover number.

We have found that these objects are achieved by a process for hydrogenating an aromatic compound in which at least one hydroxyl group is bonded to an aromatic ring or an aromatic compound in which at least one amino group is bonded to an aromatic ring, in the presence of a catalyst comprising as catalytically active component at least one metal of transition group I, VII or VIII of the Periodic Table applied to a support, wherein the catalyst is obtainable by a) dissolving the catalytically active component or a precursor compound thereof in a solvent, b) admixing the solution thus obtained with an organic polymer which is able to bind at least ten times its own weight of water, giving a swollen polymer, c) subsequently mixing the swollen polymer with a catalyst support material and d) shaping, drying and calcining the composition obtained in this way.

We have also found that these objects and possibly further objects are achieved by hydrogenation processes as are described in the subclaims. The process of the present invention is notable for the fact that the active component is, owing to the above-defined method of preparation, predominantly located in the macropores of the support, which leads to satisfactory activity and high selectivity. For the purposes of the present invention, macropores are pores whose diameter is above 50 nm and mesopores are pores whose diameter is from 2 to 50 nm, corresponding to the definition in Pure Applied Chem. 45 (1976), 79.

The term "aromatic compound in which at least one hydroxyl group is bonded to an aromatic ring" or "aromatic compound in which at least one amino group is bonded to an aromatic ring" refers to all compounds which contain a unit of the following structure (I):

where R is a hydroxyl or amino group.

If, for the purposes of the present invention, use is made of aromatic compounds in which at least one hydroxyl group and also at least one unsubstituted or substituted $C_1$–$C_{10}$-alkyl radical and/or $C_1$–$C_{10}$-alkoxy radical is bonded to an aromatic ring, the resulting ratio of cis to trans isomers can be varied within a wide range as a function of the reaction conditions (temperature, solvent). Furthermore, the compounds obtained can be further processed without further purification steps. The formation of alkylbenzenes is virtually completely avoided.

As in the case of the above-described compounds in which at least one hydroxyl group is bonded to an aromatic ring, the process of the present invention can also be used to hydrogenate aromatic compounds in which at least one amino group is bonded to an aromatic ring with high selectivity to give the corresponding cycloaliphatic compounds. What has been said above regarding the cis and trans isomers also applies to the amines which are additionally substituted by a $C_1$–$C_{10}$-alkyl radical and/or $C_1$–$C_{10}$-alkoxy radical.

In particular, the formation of deamination products, for example cyclohexanes or partially hydrogenated dimerization products such as phenylcyclohexylamines, is virtually completely avoided in this embodiment.

Furthermore, the process of the present invention gives high turnover numbers at high throughputs over the catalyst and for long catalyst operating lives. The throughput over the catalyst is here the space-time yield of the process, i.e. the amount of starting material reacted per unit time and per amount of catalyst present. Operating life is the time or the amount of reacted starting material which a catalyst copes with without its properties deteriorating and without the product properties changing significantly.

Compounds

Aromatic compounds in which at least one hydroxyl group is bonded to an aromatic ring The process of the present invention enables aromatic compounds in which at least one hydroxyl group and preferably also at least one unsubstituted or substituted $C_1$–$C_{10}$-alkyl radical and/or alkoxy radical is bonded to an aromatic ring to be hydrogenated to give the corresponding cycloaliphatic compounds. Mixtures of two or more of these compounds can also be used and the aromatic compounds can be monocyclic or polycyclic aromatic compounds. The aromatic compounds contain at least one hydroxyl group which is bonded to an aromatic ring. The simplest compound of this group is phenol. The aromatic compounds preferably have one hydroxyl group per aromatic ring and can be substituted on the aromatic ring or rings by one or more alkyl and/or alkoxy radicals, preferably $C_1$–$C_{10}$-alkyl and/or alkoxy radicals, particularly preferably $C_1$–$C_{10}$-alkyl radicals, in particular methyl, ethyl, propyl, isopropyl, butyl, isobutyl or tert-butyl radicals; among the alkoxy radicals, preference is given to the $C_1$–$C_8$-alkoxy radicals such as methoxy, ethoxy, propoxy, isopropoxy, butoxy, isobutoxy or tert-butoxy radicals. The aromatic ring or rings and also the alkyl and alkoxy radicals may be substituted by halogen atoms, in particular fluorine atoms, or bear other suitable inert substituents.

Preferably, the compounds which can be hydrogenated according to the present invention contain at least one, preferably from one to four, in particular one, $C_1$–$C_{10}$-alkyl radical which is preferably located on the same aromatic ring as the hydroxyl group or groups. Preferred compounds are (mono) alkylphenols in which the alkyl radical can be in the o, m or p position to the hydroxyl group. Particular preference is given to para-alkylphenols, also known as 4-alkylphenols, where the alkyl radical preferably has from 1 to 10 carbon atoms and, in particular, is a tert-butyl radical. Preference is given to 4-tert-butylphenol. Polycyclic aromatic compounds which can be used according to the present invention are, for example, β-naphthol and α-naphthol.

The aromatic compounds in which at least one hydroxyl group and preferably also at least one unsubstituted or substituted $C_1$–$C_{10}$-alkyl radical and/or alkoxy radical is bonded to an aromatic ring can also contain a plurality of aromatic rings which are linked via an alkylene radical, preferably a methylene group. The linking alkylene group, preferably methylene group, can bear one or more alkyl substituents which can be $C_1$–$C_{20}$-alkyl radicals and are preferably $C_1$–$C_{10}$-alkyl radicals, particularly preferably methyl, ethyl, propyl, isopropyl, butyl or tert-butyl radicals.

In these compounds, each of the aromatic rings can contain at least one bonded hydroxyl group. Examples of such compounds are bisphenols which are linked in the 4 position via an alkylene radical, preferably a methylene radical.

In the process of the present invention, particular preference is given to reacting a phenol substituted by a $C_1$–$C_{10}$-alkyl radical, preferably $C_1$–$C_6$-alkyl radical, where the alkyl radical may be substituted by an aromatic radical, or mixtures of two or more of these compounds.

In a further preferred embodiment of this process, p-tert-butylphenol, bis(p-hydroxyphenyl)dimethylmethane or a mixture thereof is reacted.

Aromatic compounds in which at least one amino group is bonded to an aromatic ring The process of the present invention also enables aromatic compounds in which at least one amino group is bonded to an aromatic ring to be hydrogenated to give the corresponding cycloaliphatic compounds. Mixtures of two or more of these compounds can also be used. The aromatic compounds can be monocyclic or polycyclic aromatic compounds and contain at least one amino group which is bonded to an aromatic ring. The aromatic compounds are preferably aromatic amines or diamines. The aromatic compounds can be substituted on the aromatic ring or rings or on the amino group by one or more alkyl and/or alkoxy radicals, preferably $C_1$–$C_{20}$-alkyl radicals, in particular methyl, ethyl, propyl, isopropyl, butyl, isobutyl or tert-butyl radicals; among the alkoxy radicals, preference is given to the $C_1$–$C_8$-alkoxy radicals such as methoxy, ethoxy, propoxy, isopropoxy, butoxy, isobutoxy or tert-butoxy radicals. The aromatic ring or rings and also the alkyl and alkoxy radicals may be substituted by halogen atoms, in particular fluorine atoms, or bear other suitable inert substituents.

The aromatic compound in which at least one amino group is bonded to an aromatic ring can also contain a plurality of aromatic rings which are linked via an alkylene group, preferably a methylene group. The linking alkylene group, preferably methylene group, can bear one or more alkyl substituents which can be $C_1$–$C_{20}$-alkyl radicals and are preferably $C_1$–$C_{10}$-alkyl radicals, particularly preferably methyl, ethyl, propyl, isopropyl, butyl, sec-butyl or tert-butyl radicals.

The amino group bonded to the aromatic ring can likewise be substituted by one or two of the above-described alkyl radicals.

Particularly preferred compounds are aniline, naphthylamine, diaminobenzenes, diaminotoluenes, bis(p-aminophenyl)dimethylmethane and bis(p-aminophenyl)methane or mixtures thereof.

Catalysts

The catalysts used according to the present invention and their preparation are known per se and are described in detail in EP-A-0 653 243, the full scope of which in respect of the catalyst used and its preparation is incorporated by reference in the present application.

Nevertheless, the principal process steps a) to d) for preparing the catalyst used according to the present invention will be described in general terms below.

The supported catalysts used according to the present invention are prepared by the following process steps:

Process step a):

The catalytically active components or their precursor compounds, i.e. the metals of transition group I, VII or VIII of the Periodic Table or mixtures of two or more of these metals, preferably ruthenium, rhodium, platinum, palladium, copper, rhenium, cobalt, nickel or a mixture of two or more thereof, in particular ruthenium alone or together with at least one metal of transition group I, VII or VIII of the Periodic Table, or their precursor compounds which are only converted into catalytically active components during further processing or activation steps, are dissolved in a solvent.

The solvent to be used is preferably water or a polar, water-miscible solvent such as an alcohol, ether or amine. Preference is given to using water or an ammonia/water mixture.

The catalytically active component is generally used in the form of a water-soluble metal salt such as a nitrate, nitrosyl nitrate or halide, or as a chloro, nitrito or amine complex. Such compounds are commercially available.

Also suitable are sols of the above-described metals, e.g. sols of the metals palladium, platinum, silver and copper as are obtainable, for example, by methods described in Angew. Chem. 103 (1991), 852 or sometimes commercially.

Furthermore, the catalyst used according to the present invention can further comprise, in addition to the catalytically active component defined above, promoters or moderators which can influence the catalytic activity or selectivity and are different from the active metal or metals. These are added directly or likewise in the form of their precursor compounds to the solution of the abovementioned metal salts of metals of transition groups I, VII and VIII of the Periodic Table or their sols.

The concentration of the above-described metals of transition groups I, VII and VIII of the Periodic Table is subject to no particular restrictions and depends on the solubility of the corresponding compound in the solvent selected. It is generally in a range from at least about 0.1 g/l to the saturation concentration of the solution. Furthermore, the amount of the active component depends on the desired concentration used in the supported catalyst used according to the present invention. The above-described solutions are generally prepared at room temperature. Further details and preferred embodiments of process step a) may be found in EP-A-0 653 234 in the section "Process step a)".

Process step b):

The above-described solutions of the catalytically active components or their precursor compounds are admixed with an organic polymer. The solution can either be added to the polymer or the polymer can be added to the solution.

The organic polymer used is capable of binding at least ten times its own weight of water. Such compounds are described as hydrogels (cf. B. D. Rathmer et al., in "Hydrogels for medical and related applications", ACS Symposium Series No. 31 (1976)). These are crosslinked polymeric compounds in which the crosslinking can be by means of ionic interactions or hydrogen bonds or by means of chemical crosslinking.

Suitable polymers are, for example, graft copolymers of starch and acrylic acid, (e.g. G. F. Fanta et al., in Starch 34 (1982), 95), starch and acrylic acid (EP-A 83 022), polysaccharides and acrylic acid (DE-A 41 05 000), copolymers of polyvinyl alcohol and sodium acrylates (U.S. Pat. No. 4,155,893), copolymers of acrylamide and acrylic acid (EP-A 72 214), crosslinked polyethylene oxide (U.S. Pat. No. 3,264,202), crosslinked polyacrylamide (U.S. Pat. No. 3,669,103), crosslinked poly-N-vinylpyrrolidone (U.S. Pat. No. 3,669,103), crosslinked polyvinylalcohol (Walter et al., Biomaterials 9 (1988), 150), crosslinked carboxycellulose fibers (U.S. Pat. No. 3,826,711), hydrolysates of polyvinyl acetate-acrylic acid copolymers (GB 20 30 990) and hydrolysates of polyacrylonitrile (U.S. Pat. No. 4,366,206).

Preference is given to using crosslinked polymers of acrylic acid, acrylic acid and acrylamide and also of acrylamide, with particular preference being given to using partially neutralized sodium polyacrylates which are weakly crosslinked, these can be crosslinked using known crosslinkers as are described in EP-A-0 653 243 under "process step b)".

In general, the polymer is admixed with as much solution of the active component as it can completely absorb. This process is generally complete in 60 minutes; the swelling of the polymer is usually carried out at room temperature. When swelling polyacrylates, the pH should be at least 6 since otherwise only insufficient absorption of solution occurs.

Further details regarding process step b) may be found in EP-A-0 653 243 under "process step b)".

Process step c):

The swollen polymer is mixed with a pulverulent catalyst support material. The order in which the components are added to one another is of no consequence. Suitable support materials are materials which are inert under the reaction conditions of the reaction to be catalyzed, with preference being given to using aluminum oxide, silicon dioxide, kieselguhr, a silica gel, an alumina, a silicate, a zeolite in admixture with an aluminum oxide, a zirconium oxide, a titanium oxide or a mixture of two or more thereof. Particular preference is given to aluminum oxides and silicon dioxide.

It is also possible to use oxides of Mg, Ca, Sr, Ba, sulfates of Ca, Ba, Sr, Pb, carbonates of Mg, Ca, Sr, Ba, Ni, Co, Mn, Fe, Cu, sulfides of Mo, W, Co, Ni, Fe, Pb, Ag, Cr, Cu, Cd, Sn, Zn, carbides of B, Si, W and nitrides of B and Si.

The amount of the support material is generally from about 10 to about 100 times, preferably from about 20 to about 200 times, that of the non-swollen polymer.

Customary peptizing agents can be added to the solution to improve the mechanical stability of the shaped bodies obtained, for example ammonia for aluminum oxide support materials and sodium hydroxide for silicon dioxide. The amount of these substances is generally from about 0.1 to about 5% by weight, based on the total weight of the support material.

The above-described components are mixed, which can be carried out using customary kneaders or compounders.

Process step d):

The composition obtained after process step c) is shaped, e.g. by extrusion in an extruder or by shaping in a ram extruder to form extrudates having the desired dimensions.

The shaped bodies obtained in this way are subsequently dried, generally at from about 100° C. to about 150° C. for from about 2 to about 24 hours.

The shaped bodies are subsequently calcined, generally for more than 2 up to about 24 hours at from about 300° C. to about 800° C., preferably from about 300° C. to 550° C. Depending on the active component, this can be followed by an activation step in which the catalytically active component is formed.

The resulting supported catalysts can also be applied in a manner known per se to nonporous supports of, for example, steatite, to glass rings, quartz rings or highly sintered aluminum oxide rings.

Further details regarding process step d) may be found in EP-A-0 653 241 under "process step d)".

The catalysts are activated by treatment in a gas stream comprising from 50 to 100% by volume of $H_2$ and from 0 to 50% by volume of $N_2$ at from about 30° C. to about 600° C., preferably from about 150° C. to about 450° C.

The resulting supported catalysts are highly porous and have a low bulk density. It can clearly be seen from electron micrographs that the major part, in general more than 80%, of the active component is located in the macropores. The proportion of the active component which is located in the macropores can be determined only by examining a plurality of representative sections through the catalyst extrudate by scanning electron microscopy using backscattering of electrons to reveal the heavy elements.

In the catalysts of the present invention, the reactants can easily reach the active centers and the reaction products can easily leave them. Locating the catalytically active components in the macropores makes it possible to prepare catalysts which, compared with conventional catalysts having the same activity, only require a fraction of the amount of active component. The amount of catalytically active component is preferably from about 0.01 to about 30% by weight, more preferably from about 0.05 to about 5% by weight and in particular from about 0.1 to about 3% by weight.

The catalyst used according to the present invention has a high reactivity, selectivity and operating life.

The process of the present invention gives the corresponding hydrogenation product in high yield and purity.

Hydrogenation

The hydrogenation is carried out at suitable pressures and temperatures. Preference is given to pressures above about $5 \times 10^6$ Pa, preferably from about $1 \times 10^7$ to $3 \times 10^7$ Pa. Preferred temperatures are in the range from about 50° C. to about 300° C., preferably from about 100° C. to about 270° C. and particularly preferably from about 150° C. to about 220° C.

The hydrogenation can be carried out continuously or batchwise, either in the downflow mode or the upflow mode. In a continuous process, part of the hydrogenation product leaving the reactor can be recirculated to the reactor feed upstream of the reactor. The amount of any such hydrogenation product leaving the reactor which is recirculated as solvent is such that the ratios indicated in the section "solvents and diluents" are achieved. The remaining amount of hydrogenation product is taken off.

When the process is carried out continuously, the amount of compound or compounds to be hydrogenated is preferably from about 0.05 to about 3 kg per liter of catalyst per hour, more preferably from about 0.1 to about 1 kg per liter of catalyst per hour.

Hydrogenation gases used can be any gases which comprise free hydrogen and do not contain any harmful amounts of catalyst poisons such as CO. For example, reformer off-gases can be used. Preference is given to using pure hydrogen as hydrogenation gas.

In the case of phenols and amines which are additionally substituted by at least one unsubstituted or substituted $C_1$–$C_{10}$-alkyl and/or $C_1$–$C_{10}$-alkoxy radical, the resulting ratio of cis to trans isomers can be varied within a wide range as a function of the reaction conditions (temperature, solvent).

If an aromatic compound in which at least one amino group is bonded to an aromatic ring is to be hydrogenated by means of the catalyst of the present invention, the hydrogenation can also be carried out in the presence of ammonia or alkylamines, for example methylamine, ethylamine, propylamine or dimethylamine, diethylamine or dipropylamine. In this case, appropriate amounts of ammonia, monoalkylamine or dialkylamine are used, preferably from about 0.5 to about 50 parts by weight, particularly preferably from about 1 to about 20 parts by weight, in each case based on 100 parts by weight of the compound or compounds to be hydrogenated. Particular preference is given to using anhydrous ammonia or anhydrous amines.

Solvents or Diluents

In the process of the present invention, the hydrogenation can be carried out in the absence of a solvent or diluent, i.e. the hydrogenation does not have to be carried out in solution.

If a solvent or diluent is employed, any suitable solvent or diluent can be used. The selection is not critical. For example, the solvents or diluents can also contain small amounts of water.

In the hydrogenation of an aromatic compound in which at least one hydroxyl group is bonded to an aromatic ring, examples of suitable solvents or diluents include the following:

Straight-chain or cyclic ethers such as tetrahydrofuran or dioxane, and also aliphatic alcohols in which the alkyl radical preferably has from 1 to 10 carbon atoms, in particular from 3 to 6 carbon atoms.

Examples of preferred alcohols are i-propanol, n-butanol, i-butanol and n-hexanol.

Mixtures of these or other solvents or diluents can likewise be used.

In the hydrogenation of an aromatic compound in which at least one amino group is bonded to an aromatic ring, examples of suitable solvents or diluents include the following:

Straight-chain or cyclic ethers such as tetrahydrofuran or dioxane, and also ammonia and monoalkylamines or dialkylamines in which the alkyl radical preferably has from 1 to 3 carbon atoms, for example methylamine, ethylamine, propylamine or the corresponding dialkylamines.

Mixtures of these or other solvents or diluents can likewise be used.

In both the above embodiments, the amount of solvent or diluent used is not subject to any particular restriction and can be freely selected according to requirements, although preference is given to amounts which lead to a 10–80% strength by weight solution of the compound to be hydrogenated.

In the process of the present invention, particular preference is given to using the product formed in the hydrogenation of this process as solvent, if desired together with other solvents or diluents. In this case, part of the product formed in the hydrogenation process can be mixed into the compounds to be hydrogenated. The amount of hydrogenation product mixed in as solvent or diluent is preferably from 1 to 30 times, particularly preferably from 5 to 20 times, in particular from 5 to 10 times, the weight of the aromatic compounds to be hydrogenated.

The invention is illustrated below by means of some examples.

EXAMPLES

Preparation of catalyst A (1 % by weight $Ru/Al_2O_3$)

14.2 g of a nitric acid solution of ruthenium nitrosyl nitrate (14% by weight of Ru) were admixed with 150 ml of water and 6 g of a high molecular weight sodium polyacrylate (90% of the acid groups neutralized, crosslinked with 0.4 mol % of polyethylene glycol having a molar mass of 1,500) which can bind 300 times its own weight of water. After 30 minutes, the gel-like mass was kneaded with 280 g of $Al_2O_3$ (pseudo-boehmite, BET surface area after calcination at 600° C.: 300 $m^2/g$). After addition of 200 ml of ammonia solution (containing 50 ml of concentrated ammonia), the mixture was kneaded for 1 hour. The mixture was shaped at $6.5\times10^6$ Pa (65 bar) in a ram extruder to form 3.8 mm extrudates, dried for 16 hours at 120° C. and calcined for 6 hours at 300° C.

The resulting catalyst had the following properties:

| | |
|---|---|
| Bulk density: | 425 g/l |
| BET surface area: | 294 $m^2/g$ |
| Pore volume (DIN 66 132) | 0.81 ml/g |
| Mean diameter of the macropores [nm]: | 1,000 |
| Mean diameter of the mesopores [nm]: | 6 |
| Proportion of macropores [% by volume] | 35 |

The pore volume was determined in accordance with DIN 66 132 by mercury porosimetry as per the teachings of J. V. Brakel et al., Powder Technology 29 (1991), 1.

Example 1

1.2 l of the above-described catalyst were placed in an electrically heated flow reactor. The hydrogenation of aniline was then commenced at $2\times10^7$ Pa (200 bar) and 160° C. without prior activation. The hydrogenation was carried out continuously in the upflow mode, with part of the hydrogenation product being recirculated via a circulation pump and mixed into the feed upstream of the reactor. In this way, an amount of hydrogenation product which was 10 times the amount of aniline was added as solvent. At the top of the separator, 500 l/h to 600 l/h of hydrogen were depressurized. The amount of aniline which was fed continuously to the reactor corresponded to a throughput over the catalyst of 1.0 kg/l·h.

Depending on the reaction temperatures, the following product compositions were obtained under steady-state reaction conditions (both here and in the following tables "%" refers to the gas chromatographic percentage areas of the respective product peaks):

TABLE 1

| Temperature °C. | CHA[1] % | DCHA[2] % | Aniline % | Cyclohexane + Cyclohexene % |
|---|---|---|---|---|
| 160 | 99.1 | 0.45 | 0.10 | 0.04 |
| 180 | 97.0 | 2.75 | 0.06 | 0.06 |
| 200 | 95.9 | 3.9 | — | 0.09 |

[1]CHA = Cyclohexylamine;
[2]DCHA = Dicyclohexylamine

Example 2

A hydrogenation was carried out as described in Example 1, but, in addition, anhydrous ammonia was metered in continuously. 10 parts by weight of ammonia were added per 100 parts by weight of aniline. Depending on the reaction temperatures, the following product compositions were obtained under steady-state reaction conditions:

TABLE 2

| Temperature °C. | CHA[1] % | DCHA[2] % | Aniline % | Cyclohexane + Cyclohexene % |
|---|---|---|---|---|
| 180 | 99.3 | 0.08 | — | 0.07 |
| 200 | 98.4 | 0.8 | — | 0.09 |

[1]CHA = Cyclohexylamine;
[2]DCHA = Dicyclohexylamine

Example 3

2 kg of a solution of 50% by weight of tolylenediamine (2,4- and 2,6-diaminotoluene isomer mixture) in tetrahydrofuran and 500 ml of the above-described catalyst were introduced into a 3.5 l pressure autoclave.

Hydrogenation was subsequently carried out batchwise at 150° C. and $2 \times 10^7$ Pa (200 bar) for 5 hours. The conversion to the desired cycloaliphatic diamine isomer mixture was quantitative and the residual aromatics content was less than 0.01% by weight.

Example 4

150 ml of a solution of 50% of p-tert-butylphenol in butanol and 15 ml of the above-described catalyst were placed in a 0.3 l stirring autoclave.

Hydrogenation was subsequently carried out at 200° C. for 6 hours. The conversion to 4-tert-butylcyclohexanol was quantitative, the selectivity was 99.2% at a cis/trans ratio of 48/52.

Example 5

150ml of a solution of 50% of bisphenol A in butanol and 15 ml of the above-described catalyst were placed in a 0.3 l stirring autoclave.

Hydrogenation was subsequently carried out at 200° C. for 6 hours. The conversion was quantitative, the selectivity to 2,2-bis(4-hydroxycyclohexyl)propane was 98.7%.

We claim:

1. A process for hydrogenating an aromatic compound in which at least one hydroxyl group is bonded to an aromatic ring or an aromatic compound in which at least one amino group is bonded to an aromatic ring, in the presence of a catalyst comprising as catalytically active component at least one metal of transition group I, VII or VIII of the Periodic Table applied to a support, wherein the catalyst is obtainable by a) dissolving the catalytically active component or a precursor compound thereof in a solvent, b) admixing the solution thus obtained with an organic polymer which is able to bind at least ten times its own weight of water, giving a swollen polymer, c) subsequently mixing the swollen polymer with a catalyst support material and d) shaping, drying and calcining the composition obtained in this way.

2. A process as claimed in claim 1, wherein the catalytically active component or components is/are selected from the group consisting of ruthenium, rhodium, platinum, palladium, copper, rhenium, cobalt, nickel and mixtures of two or more thereof.

3. A process as claimed in claim 1, wherein the content of the catalytically active components is from 0.01 to 30% by weight, based on the total weight of the catalyst.

4. A process as claimed in claim 1, wherein the support is an aluminum oxide, silicon dioxide, kieselguhr, a silica gel, an alumina, a silicate, a zeolite in admixture with an aluminum oxide, a zirconium oxide, a titanium oxide or a mixture of two or more thereof.

5. A process as claimed in claim 1, wherein an aromatic compound in which at least one hydroxyl group is bonded to an aromatic ring and, in addition to the hydroxyl group or groups, at least one $C_1$–$C_{10}$-alkyl group or at least one $C_1$–$C_{10}$-alkoxy group or at least one $C_1$–$C_{10}$-alkyl group and at least one $C_1$–$C_{10}$-alkoxy group, each of which may in turn be substituted, is/are bonded to an aromatic ring, or an aromatic compound in which at least one amino group is bonded to an aromatic ring and, in addition to the amino group or groups, at least one $C_1$–$C_{10}$-alkyl group or at least one $C_1$–$C_{10}$-alkoxy group or at least one $C_1$–$C_{10}$-alkyl group and at least one $C_1$–$C_{10}$-alkoxy group, each of which may in turn be substituted, is/are bonded to an aromatic ring, is hydrogenated.

6. A process as claimed in claim 1, wherein the hydrogenation is carried out in the presence of a solvent or diluent.

* * * * *